United States Patent [19]

Cotey et al.

[11] Patent Number: 5,009,657
[45] Date of Patent: Apr. 23, 1991

[54] UMBILICAL CORD CUTTING AND CLAMPING DEVICE

[75] Inventors: John Cotey, Haddonfield, N.J.; Mohammed S. Jahanger, 500 Egg Harbor Rd., Turnersville, N.J. 08012

[73] Assignee: Mohammed S. Jahanger, Turnersville, N.J.

[21] Appl. No.: 450,743

[22] Filed: Dec. 14, 1989

[51] Int. Cl.⁵ .............................................. A61B 17/32
[52] U.S. Cl. .................... 606/120; 606/142; 606/167; 606/174
[58] Field of Search ............... 606/120, 142, 174, 210, 606/205-208, 167

[56] References Cited

U.S. PATENT DOCUMENTS

| | | |
|---|---|---|
| 640,517 | 1/1900 | Achesom . |
| 2,052,870 | 9/1936 | Coco . |
| 2,060,724 | 10/1936 | Carroll . |
| 2,384,697 | 9/1945 | Riccardi . |
| 3,006,344 | 10/1961 | Vogelfanger . |
| 3,166,071 | 1/1965 | Mayer . |
| 3,323,208 | 6/1967 | Hurley ................................ 606/120 |
| 3,367,336 | 2/1968 | Eizenberg ........................... 606/210 |
| 3,503,398 | 3/1970 | Fogarty et al. . |
| 3,631,858 | 1/1972 | Ersek . |
| 3,783,875 | 1/1974 | Winshel . |
| 3,921,640 | 11/1975 | Freeborn . |
| 3,981,308 | 9/1976 | Schlein . |
| 4,390,019 | 6/1983 | LeVeen et al. . |
| 4,428,374 | 1/1984 | Auburn . |
| 4,434,795 | 3/1984 | Mericle . |
| 4,572,181 | 2/1986 | Mattler . |
| 4,602,629 | 7/1986 | Schnirman . |
| 4,671,282 | 6/1987 | Tretbar . |
| 4,672,966 | 6/1987 | Haas, Jr. . |
| 4,870,965 | 10/1989 | Jahanger . |

FOREIGN PATENT DOCUMENTS 934296  7/1961  United Kingdom .

OTHER PUBLICATIONS

Jarit Surgical Instrument Catalog, p. 176, (1987).

Primary Examiner—Michael H. Thaler
Attorney, Agent, or Firm—Paul & Paul

[57] ABSTRACT

An umbilical cord cutting and clamping device is used with a fetal cord end clip to permit a physician to quickly sever an umbilical cord and securely clamp the fetal cord end. The clip is retained in the device until the cord end has been securely clamped. As the device and clip are closed on an umbilical cord, a tab formed on the central section of the clip rotates out from under a lug formed on the device to release the rear of the clip from the device.

4 Claims, 3 Drawing Sheets

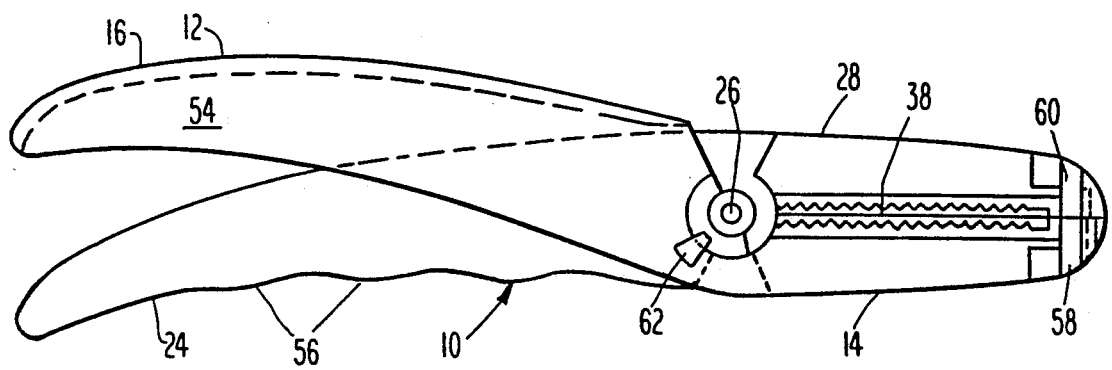
Fig. 3
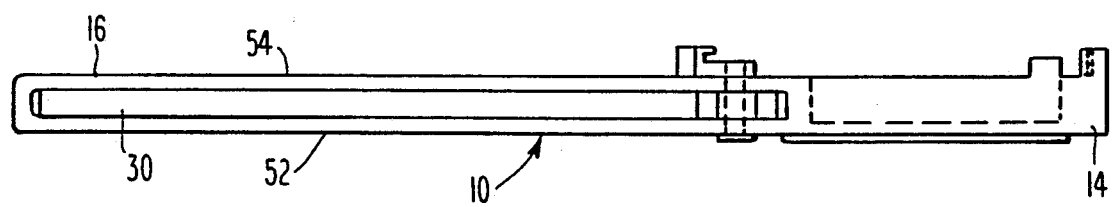
Fig. 4
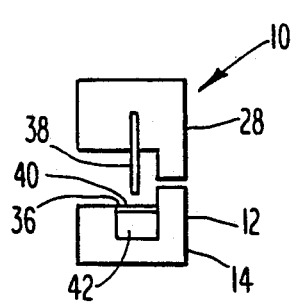
Fig. 10
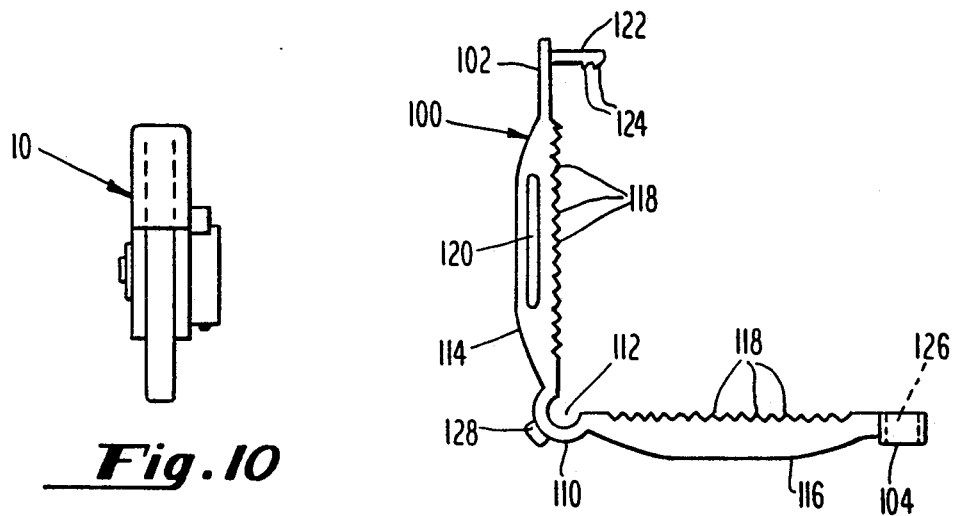
Fig. 5
Fig. 11
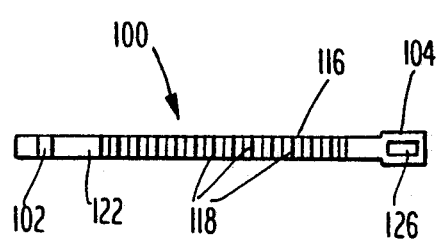
Fig. 6

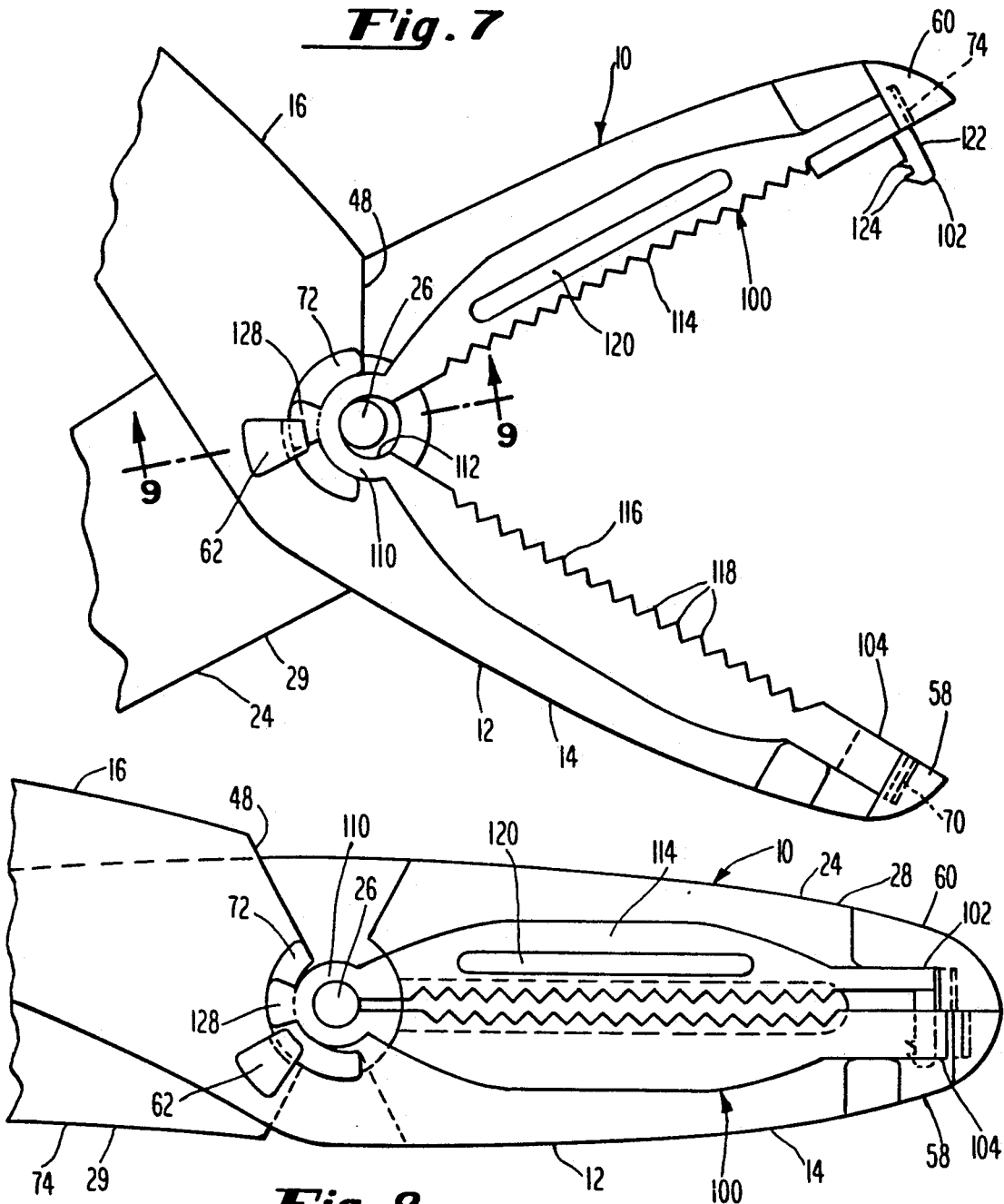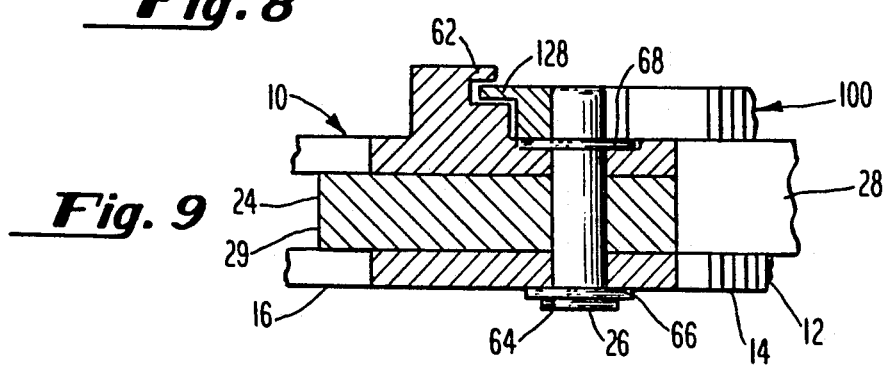

UMBILICAL CORD CUTTING AND CLAMPING DEVICE

BACKGROUND OF THE INVENTION

1. Field of the Invention

The present invention relates generally to obstetrical instruments and more particularly to a device for simultaneously cutting and clamping an umbilical cord and to clips for use in combination with the device.

2. Brief Description of the Prior Art

Surgical instruments for simultaneously severing and clamping the umbilical cord of a new born infant are known. For example, U.S. Pat. Nos. 640,517, 2,052,870, 2,060,764, 3,166,071 and 4,428,374 each disclose clamping devices for simultaneously cutting the umbilical cord and clamping ends of the cord. The devices generally employ clamps which are detachable or removable from the clamping device after the cord has been severed and detached. U.S. Pat. No. 3,631,858 discloses a device for simultaneously clamping and severing the umbilical cord in a single operation requiring only one hand, non-detachable clamps being employed. U.S. Pat. No. 4,646,401 discloses a scissors-like surgical instrument for severing the umbilical cord employing a single-use, disposable blade assembly to sever the cord.

In general it is desirable in obstetrical practice to sever and securely clamp both ends, especially the fetal end, of the severed umbilical cord as quickly as possible. This is especially so when complications arise during delivery, such as when the umbilical cord is wrapped around the infant's neck. The fetal end of the cord must be securely clamped so that during the drying and consequent shrinkage of the cord, which occurs after delivery, further bleeding, infection, or umbilical hernia, do not occur.

While the cord is being cut and clamped, it must be securely held within the device, as must the clip or clips applied to the cord ends. Ideally, the cord ends should be separable immediately after cutting and clamping. Some prior art devices employ means for securing the clips such that the clip must be released from the device after the cord end is clamped. This additional operation may require the physician's second hand, possibly preventing him or her from performing other tasks associated with the delivery. There is a need for a surgical instrument which can be reliably operated using a single hand to cut an umbilical cord and clamp the cord ends, especially the fetal cord end, thereby minimizing the time which the obstetrician must expend in cutting and clamping the cord. Further, there is a need for a device in which a cord clip can be readily installed and is reliable and securely held while the cord is being cut and clamped, and from which the clamped end of the fetal cord is released and readily separably from the device after the cord has been cut.

SUMMARY OF THE INVENTION

The present invention provides an umbilical cord cutting and clamping device for severing an umbilical cord to form a maternal cord end or a fetal cord end, and for clamping the fetal cord end. The device is adapted for use with a fetal cord end clip. Advantageously, the invention provides a physician with the means for quickly severing an umbilical cord and securely clamping the fetal cord end, thereby reducing the risks associated with hemorrhaging of the cord end and infection.

The clip comprises a pair of elongated arms extending from a central section having an opening formed therein. Each arm has a generally straight inner surface having teeth formed thereon for grasping the surface of the fetal cord end. Each arm also has lock means formed proximate the end thereof for locking together the arms when the clamp is closed. At least one of the arms has an elongated aperture formed therein for cushioning the force exerted on an umbilical cord when the clamp is closed on the cord end. The central section of the clip includes a clip positioning means for retaining the clip in the device until the fetal cord end has been clamped.

The device comprises an integral first jaw-and-handle means and an integral second jaw-and-handle means, the two jaw-and-handle means being pivotably affixed together. The first jaw-and-handle means includes a first clamping means for clamping the maternal cord end, first severing means for severing the umbilical cord, and first support means for supporting and positioning a first end of the fetal cord end clip until the fetal cord end has been clamped by the clip.

Similarly, the integral second jaw-and-handle means includes a second clamping means for clamping the maternal cord end, a second severing means for severing the umbilical cord, and second support means for supporting and positioning a second end of the clip until the fetal cord end has been clamped by the clip. In addition, the second jaw-and-handle means includes a rear retention means for supporting the central section of the fetal cord end clip until the fetal cord end has been clamped by the clip. Each jaw-and-handle means includes a jaw and a handle.

In the device, the two jaw-and-handle means are rotatable by a physician with respect to one anther from an open position in which the fetal cord end clip can be installed in the device to a closed position.

In a presently preferred embodiment, the clip is installed in the device and the resulting unit is sterilized and packaged with the device in the open position. The package is opened under sterile conditions during delivery just before the cord is to cut, and the fetal cord end clip and the device are discarded after use.

In the device a pivot means affixes the first and second jaw-and-handle means, and the pivot means extends outwardly from and generally perpendicular to the second jaw-and-handle means. This pivot means is adapted to being received by the opening in the central section of the clip.

The rear retention means of the device retains the clip positioning means of the clip to retain the central section of the clip in the device when the clip is installed in the device and the device is in the open position. In a presently preferred embodiment, the clip positioning means comprises a generally planar tab extending outwardly from the central section of the clip, and the rear retention means includes a generally planar lug extending generally inwardly toward the pivot means. The tab is positioned under the lug when the clip is installed in an open device.

As the device is closed, the clip positioning means rotates with respect to the rear retention means to release the clip from the device after the fetal cord end has been clamped and the clip arms have been locked. In the presently preferred embodiment, the tab rotates out from under the lug as the device is closed.

Preferably, the device further includes a plurality of elongated teeth extending from the jaw of one of the jaw-and-handle means, and a plurality of apertures in the other jaw-and-handle means for receiving corresponding ones of the elongated teeth. As the device is closed, one or more of the teeth can puncture the umbilical cord and thereby aid in securing the device to the cord and resisting slippage as the cord is cut. As the device is closed, the teeth enter the respective apertures and thereby maintain alignment of the jaws as the device is closed about the umbilical cord.

It is also preferred that the first severing means include a blade and the second severing means include an anvil. The anvil preferably comprises a thin section of plastic material extending over an elongated opening formed in the jaw of the second jaw-and-handle means. As the device is closed, the blade initially presses the cord against the thin sheet, then cuts the cord, and subsequently cuts the thin sheet. Because the thin sheet of the anvil is severed, once used, the device can not be reused. This strongly discourages reuse of this device and advantageously promotes use of a new, sterile device for each cord which must be cut.

The present invention advantageously provides the obstetrician with a means of accomplishing in less than a second a series of precedures (including cutting the umbilical cord and clamping the fetal cord end) which could otherwise take as long as five or six minutes. This permits the physician to act quickly, an important advantage during a medical crisis, as when a caesarian section is being performed because of fetal heart disorders caused by looping of the umbilical cord around the neck of the infant, or other complications. In such cases, even a few seconds delay in cutting the umbilical cord may be fatal to the infant. The device and associated clip also help prevent bleeding of the cut cord ends and infection.

Because the device of the present invention can be easily constructed to be disposable after a single use, additional protection can be provided to the obstetrician, other medical personnel, and other patients including new born infants, when an infant has been delivered by a mother known or suspected to be suffering from an infectious disease such as AIDS.

Other objects and advantages of the present invention will become readily apparent to those skilled in the art from a reading of the following brief description of the drawings, the detailed description of the preferred embodiments, and the appended claims and drawings.

BRIEF DESCRIPTION OF THE DRAWINGS

FIG. 3 is an elevational view of the device of FIG. 1 in a fully closed position viewed from the right or fetal side.

FIG. 4 is a bottom plan view of the device of FIG. 1.

FIG. 5 is a side elevational view of a fetal cord end clip for use with the device of FIG. 1, the clip being shown in open position before being installed in the device.

FIG. 6 is a top plan view of the clip of FIG. 5.

FIG. 7 is an enlarged, fragmentary view of the device of FIG. 1 shown in the fully open position from the right or fetal side with the clip of FIG. 5 installed therein.

FIG. 8 is an enlarged, fragmentary view of the device and clip of FIG. 7 in the fully closed position.

FIG. 9 is a fragmentary sectional view of the device and clip of FIG. 8 taken along the line 9—9.

FIG. 10 is a rear elevational view of the device of FIG. 1 in the fully closed position.

FIG. 11 is a sectional view taken along the line 11—11 of FIG. 2.

DETAILED DESCRIPTION OF THE PREFERRED EMBODIMENTS

Figure 1:
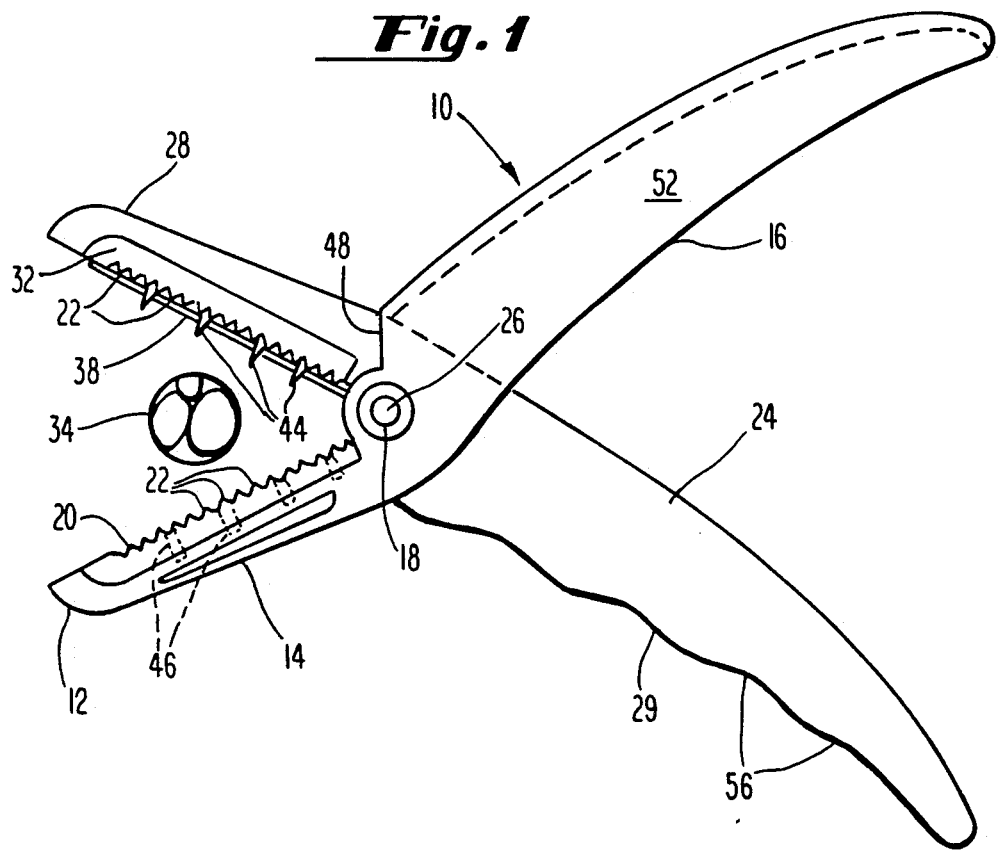
FIG. 1 is an elevational view of a presently preferred embodiment of an umbilical cord cutting and clamping device according to the present invention in a open position viewed from the left or maternal side.

Referring now to the drawings in detail, wherein like referenced numerals indicate like elements in each of the several views, reference is first made to FIG. 1, wherein an umbilical cord cutting and clamping device 10 according to the present invention is depicted. The device 10 in FIG. 1 is depicted from the left or maternal side. In the present embodiment, the device 10 is adapted to be oriented relative to the umbilical cord to be severed so that the maternal cord end, that is, the end of the umbilical cord connected to the placenta, extends from the side of the device 10 shown in FIG. 1. However, the selection of the left side of the device 10 as the maternal side is arbitrary, and a device according to the present invention in which the opposite side of the device is the maternal side can easily be constructed.

The device 10 is preferably constructed of a strong, substantially rigid material which is capable of transmitting sufficient force to cleanly sever the umbilical cord and securely clamp the fetal cord end. For example, most of the components of the device 10 can be fabricated from a suitable grade of polypropylene, Delrin ® acetal resin, or a similar material, by injection molding or a similar process. The device 10 is preferably manufactured so that it can be sterilized after a fetal cord end clip is installed, packaged in a sterile package, and discarded after a single use. Preferably, the materials from which the device 10 is fabricated are selected so that the device 10 can be readily sterilized using conventional techniques.

FIG. 1 depicts the device 10 in a fully open position. The device 10 includes an integral first jaw-and-handle means 12, preferably molded as a single piece. The first jaw-and-handle means 12 comprises a first jaw 14 and first handle 16 with a first pivot-receiving opening 18 therebetween. The first jaw 14 includes a first clamping means 20 having a plurality of teeth 22 formed on a generally straight surface on an interior or upper surface of the first jaw 14.

As shown in FIG. 1, an integral second jaw-and-handle means 24 is pivotably affixed by a pivot member or pivot 26 to the first jaw-and-handle means 12. The second jaw-and-handle means 24 includes a second jaw 28 and a second handle 29 with a second pivot-receiving aperture (not shown) therebetween. The second jaw 28 includes a second clamping means 32 having a plurality of teeth 22 formed on a generally straight interior or lower surface. In use, the open jaws 14, 28 of the device are positioned so that the umbilical cord 34 to be severed is positioned therebetween, and the handles 16, 29 are manually closed together by the physician. As the jaws 14, 28 come together, the first and second clamping means 20, 32 cooperate to clamp the cord 34 therebetween.

As best seen in the sectional view of FIG. 11, the first jaw-and-handle means 12 also includes a first severing means or anvil 36 and the second jaw-and-handle means 24 includes a second severing means or blade 38. As the device 10 is closed, the blade 38 and anvil 36 cooperate to sever the cord 34. The anvil 36 includes a thin sheet 40 of rigid plastic material, such as about 0.040 inch thick, covering an elongated aperture or recess 42 formed in the upper or inner surface of the first jaw 14. As the jaws 14, 28 are closed, the blade 38 initially presses the cord 34 against thin sheet 40, and subsequently cuts into and through the cord 34. Finally, the blade 38 cuts through the thin sheet 40, advantageously making the device 10 difficult or impossible to reuse to cut another umbilical cord. If desired, the anvil can include a section of channel stock having a "U"-shaped cross section positioned in the elongated aperture 42 (not shown) such that the central wall of the channel stock faces upward toward the blade 38, the central wall of the channel stock being severed when the device 10 is closed. In this manner, the device 10 can be reused by replacing the section of channel stock and sterilizing the device 10 with a new clip 100 installed therein.

The second jaw 28 further includes a plurality of elongated teeth 44 positioned in the second clamping member 30 parallel to the blade 38. The first jaw 14 includes a plurality of apertures 46 (best seen in FIG. 2) for receiving corresponding ones of the elongated teeth 44. As the jaws 14, 28 are closed, one or more of the elongated teeth 44 may penetrate the cord 34 and aid in pushing and securing the cord 34 within the jaws 14, 28 of the device 10. As the jaws 14, 28 are closed, the elongated teeth 44 are received by and positioned within the respective apertures 46, thereby aiding in maintaining alignment of the jaws 14, 28 in a common plane as the jaws 14, 28 are closed about the cord 34, and resisting any tendency for the jaws 14, 28 to slip or deform our of that common plane, which may otherwise reduce the amount of useful force which can be brought to bear by the obstetrician using the device 10 to sever the cord 34.

Figure 2:
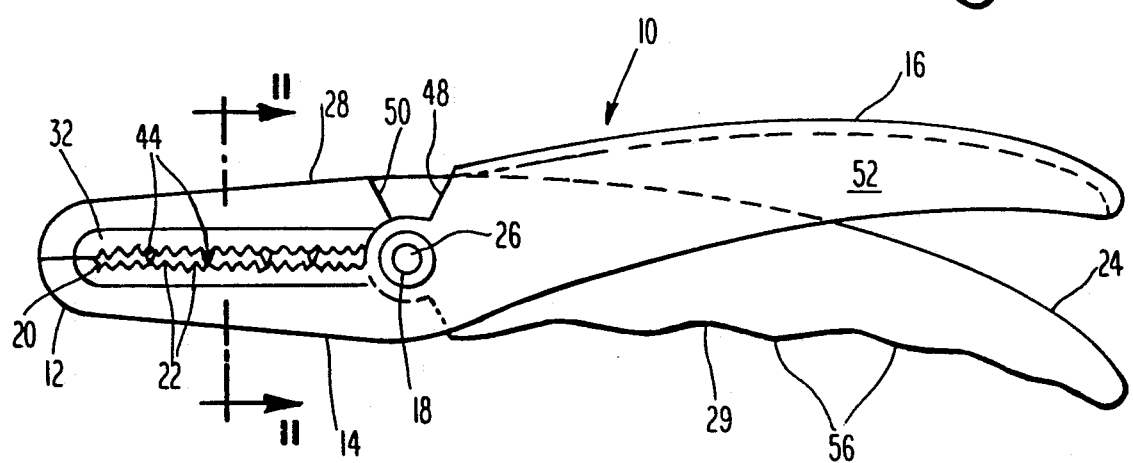
FIG. 2 is an elevational view of the device of FIG. 1 in a fully closed position viewed form the left side.

FIG. 2 depicts the device 10 in the fully closed position as seen from the left or maternal side. However, for clarity no umbilical cord is shown. As best seen by comparing FIGS. 1 and 2, the extent to which the device 10 can be opened is limited by engagement of a forward edge 48 of the first handle 16 with a shoulder 50 formed in the second jaw 28. As best seen in the bottom plan view of FIG. 4, the first handle 16 is generally "U"-shaped in section, having a pair of spaced, parallel sides 52, 54; the sides 52, 54 being spaced to permit the second handle 29 to move freely therebetween. As seen in FIGS. 1-3, the second handle 29 has a series of undulations 56 formed on its lower edge, the undulations 56 being sized and positioned to permit the device 10 to be comfortably and securely gripped by hand. Similarly, the upper surface of the first handle 16 is gently curved to accommodate the hand of the physician.

A suitable fetal cord end clamping means or clip 100 is illustrated in FIGS. 5 and 6. The fetal cord end clip 100 includes an arcuate central section 110 having a first central opening or aperture 112 formed therein, and a first or upper clamp arm 114 and a second or lower clamp arm 116 extending therefrom. The inner surfaces of the clamp arms 114, 116 are generally straight and have a plurality of teeth 118 formed thereon for contacting and gripping the severed fetal end of of the umbilical cord. The upper clamp arm 114 has formed therein an elongated aperture 120 to provide a cushioning effect when the clip 100 is closed upon a fetal cord end. A similar aperture can be provided in the lower clamp arm 116 (not shown). An inwardly directed locking tab 122 is provided proximate the end 102 of the first arm 114 opposite the central section 110. The locking tab 122 has a pair of protrusions or projections 124 extending in the plane defined by the clamp arms 114, 116. A lock aperture 126 is formed in the end 104 of the second clamp arm 116 opposite the central section 110. The locking tab 122 is sized and positioned to be securely received when the clip 100 is closed by the lock aperture 126, the pair or protrusions 124 defining a locked position for the clip 100. The central section 110 is generally arcuate and has formed therein a generally arcuate central opening or aperture 112 adopted to mount the central section 110 on the device 10. Protruding outwardly from the central section 110 of the clip 100 is a generally planar clip positioning means or tab 128.

The clip 100 is preferably formed from a sterilizable substantially rigid but somewhat deformable material such a suitable grade of polypropylene, high density polyethylene, or the like. As seen in FIG. 5, the generally flat first clamp arm 114 and the second clamp arm 116 roughly form a right angle with respect to one another when the clip 100 is in a relaxed or uncompressed state. The generally arcuate central or spring section 112 of the clip 100 functions as a spring member to oppose forces tending to close the clip 100 shut. The upper clamp arm 114, the lower clamp arm 116, and the central section 110, are generally flat and lie in a single plane, as best seen in FIG. 6.

The device 10 is depicted in FIG. 3 in the fully closed position as seen from the right or fetal side. As shown in FIG. 3, the first or lower jaw 14 has a first supporting means 58 formed proximate the forward end of the jaw 14 for supporting and positioning the first 104 end of the clip 100. In addition, the lower jaw 14 includes a rear retention means or lug 62 for supporting and positioning the central section 110 of the clip 100 until the clip 100 has been securely clamped on the fetal cord end. The second or upper jaw 28 similarly has a second support means 60 for supporting and positioning the second end 102 of the clip 100.

As best seen in the fragmentary sectional view of FIG. 9, the pivot member 26 protrudes from the fetal side of the device 10 by a distance approximately the same as the thickness of the clip 100. The pivot member 26 has an elongated head 64 formed at one end by conventional means, such as cold-heading. A first washer 66 is positioned on the pivot member 26 between the elongated head 64 and the exterior surface of the maternal side of the first jaw-and-handle means 12. A second washer 68 is positioned in a recess formed on the exterior surface of the maternal side of the first jaw-and-handle means 12 to lock the pivot member 26 in place, as by forcing the second washer 68 over the pivot member 26 to seat in an exterior circumferential groove formed on the pivot member 26, the second washer 68 having an interior diameter slightly less than the exterior diameter of the shank of the pivot member or pin 26.

FIG. 7 is an expanded, fragmentary elevational view of device 10 of FIG. 1 shown in the fully open position from the fetal or right side with a clip 100 installed therein. The clip 100 must be compressed slightly to mount the clip 100 in the device 10 when the device 10 is in the fully open position. As best seen in FIGS. 7 and 9, the tab 128 of the clip 100 is retained under the lug 62 when the device 10 is fully open. In addition, the first end 102 60 is retained by one of the clip support means of the clip 100, and the second end 104 of the clip 100 is retained by the other clip support means 58. When installing the clip 100 in the device 10 the central section 110 of the clip 100 is placed over the protruding portion of the pivot member 26, while the clip ends 102, 104 are positioned in a pair of respective recesses or slots 70, 74 formed in the first and second support means 58, 60 of the device 10 and retained therein.

As the device 10 is closed, the tab 128 of the clip 100 rotates out from under lug 62 of the device 10, and the first and second ends 102, 104 of the clip 100 are drawn out of the respective recesses 70, 74 of the first and second support means 60, 58 of the device 10 when the clip 100 has been closed and locked. The tab 128 rotates over a shoulder 72 formed in the outer surface of the first jaw-and-handle means 12.

As shown in FIG. 1 the umbilical cord 34 is placed between the jaws 14, 28 of the device 10, when the device 110 is in the fully open position, the clip 100 having been previously installed in the device 10. Subsequently, the operator manually closes the device 10 by simultaneously grasping and bringing together the first and second handles 16, 29 to force the jaws 14, 28 together to sever the umbilical cord 34, and clamp the maternal end of the umbilical cord 34 between the first and second clamping means 20, 32 of the device 10, and the fetal cord end between the first and second clamp arms 114, 116 of the clip. As the device is closed, the clip arms 114, 116 lock about the fetal cord end, and then the clip ends 102, 104 are released from the first and second support means 60, 58 and the tab 128 is released from under the device lug 62, thereby permitting the closed 10 to be moved easily away from the clamped fetal cord end.

Various modifications can be made in the details of the embodiments of the umbilical cord cutting and clamping device 10 and fetal cord end clip 100 of the present invention, all within the spirit and scope of the appended claims.

We claim:

1. In combination, an umbilical cord cutting and clamping device for severing an umbilical cord to form a maternal cord end and fetal cord end, and for clamping the fetal cord end, and a fetal cord end clip which is detachable from the device;

the clip comprising: a pair of elongated arms extending radially from a central section having an opening formed therein, each arm having teeth formed thereon and lock means formed proximate the end thereof for locking together the arms when the clip is closed, at least one arm having an elongated aperture formed therein for cushioning the force exerted on an umbilical cord when the clip is closed on the cord end, the central section including a clip positioning means for retaining the clip in the device until the cord end has been clamped;

the device comprising:

an integral first jaw-and-handle means, the first jaw-and-handle means including a first clamping means for clamping the maternal cord end, first severing means for severing the umbilical cord, and first support means for supporting and positioning a first end of the clip until the cord end has been clamped by the clip, and a rear retention means for supporting and positioning the central section of the clip until the cord end has been clamped by the clip, and an integral second jaw-and-handle means, the second jaw-and-handle means including a second clamping means for clamping the maternal jaw end, second severing means for severing the umbilical cord, second support means for supporting and positioning a second end of the clip until the cord end has been clamped by the clip;

the first jaw-and-handle means being rotatably affixed by pivot means to the second jaw-and-handle means, the pivot means extending outwardly from and generally perpendicular to the second jaw-and-handle means, the pivot means being adapted for being received by the opening of the central section of the clip, the first jaw-and-handle means being rotatable around the pivot means from an open position to a closed position;

the rear retention means of the device retaining the clip positioning means of the clip to retain the central section of the clip in the device when the clip is installed in the device and the device is in the open position, the clip positioning means rotating with respect to the rear retention means to release the clip from the device after the fetal cord end has been clamped and the clip arms have been locked.

2. A combination according to claim 1 wherein the clip positioning means comprises a generally planar tab extending outwardly from the central section of the clip, and the rear retention means includes a generally planar lug extending generally inwardly toward the pivot means, the tab being positioned under the clip as installed in an open device, the tab rotating out from under the lug as the device is closed.

3. The combination of claim 1 wherein the device further includes a plurality of elongated teeth extending form the jaw of one of the jaw-and-handle means, and a plurality of apertures in the jaw of the other jaw-and-handle means for receiving corresponding ones of the elongated teeth, the teeth entering the respective apertures as the device is closed, and thereby aiding in maintaining alignment of the jaws as the device is closed about an umbilical cord.

4. The combination of claim 1, wherein the first severing means includes a blade and the second severing means includes an anvil, the anvil comprising a thin section of plastic material extending over an elongated opening formed in the jaw of the second jaw-and-handle means, the blade initially pressing the cord against the thin sheet, thereafter cutting the cord, and subsequently cutting the thin sheet, as the device is closed.

* * * * *

UNITED STATES PATENT AND TRADEMARK OFFICE
CERTIFICATE OF CORRECTION

PATENT NO. : 5,009,657

DATED : April 23, 1991

INVENTOR(S) : John Cotey, et al.

It is certified that error appears in the above-identified patent and that said Letters Patent is hereby corrected as shown below:

Col. 7, Line 4, after 102, delete "60" and substitute therefore --of the clip 100--

Col. 7, Line 5, delete "of the clip 100" and substitute therefore --60--

Col. 7, Line 36, delete "device"

Col. 7, Line 37, after the word "closed," and before the number "10", insert --device--

Signed and Sealed this

Fifteenth Day of September, 1992

*Attest:*

DOUGLAS B. COMER

*Attesting Officer*     *Acting Commissioner of Patents and Trademarks*